United States Patent [19]
Bugaut et al.

[11] Patent Number: 4,736,067
[45] Date of Patent: Apr. 5, 1988

[54] NEW DIMETHYL DERIVATIVES OF 3-NITRO-4-AMINOANILINE, PROCESS FOR THEIR PREPARATION AND THEIR USE FOR DYEING KERATINIC FIBERS

[75] Inventors: Andrée Bugaut, Boulogne Billancourt; Alain Genet, Neuilly Plaisance; Jean Cotteret, Limay; Alex Junino, Aulnay Sous Bois, all of France

[73] Assignee: L'Oreal, Paris, France

[21] Appl. No.: 647,755

[22] Filed: Sep. 6, 1984

[30] Foreign Application Priority Data

Sep. 8, 1983 [FR] France ................ 83 14337
Aug. 23, 1984 [FR] France ................ 84 13147

[51] Int. Cl.⁴ ............... C07C 87/58; C07C 87/28; A61K 7/13
[52] U.S. Cl. ................. 564/441; 564/368; 564/369; 8/407; 8/415
[58] Field of Search ........... 564/441, 368, 369; 8/407, 415

[56] References Cited

U.S. PATENT DOCUMENTS 3,446,567 6/1969 Augustin et al. ............ 8/415
3,973,900 8/1976 Husemeyer et al. .......... 8/414
4,470,826 9/1984 Bugaut et al. ............. 564/441

FOREIGN PATENT DOCUMENTS 0075242 3/1983 European Pat. Off. .

OTHER PUBLICATIONS

Friele, L. F. C., The Journal of the Society of Dyers and Colourist, vol. 79, pp. 623–631.
Code de Solidite des Teintures et Impressions Sur Textiles, 1973, cover page and p. 29.
Nickerson, D. and Keith F. Stultz, Journal of the Optical Society of America, vol. 34, No. 9, 1964, pp. 550–570.
Webster's Dictionary, 1961, pp. 448–450.
Official Digest, 1964, pp. 373, 377.

Primary Examiner—Glennon H. Hollrah
Assistant Examiner—John A. Sopp
Attorney, Agent, or Firm—Fleit, Jacobson, Cohn & Price

[57] ABSTRACT

New dimethyl derivatives of 3-nitro-4-aminoaniline, process for their preparation, and their use for dyeing keratinic fibres.

The invention relates to dimethyl derivatives of 3-nitro-4-aminoaniline of formula:

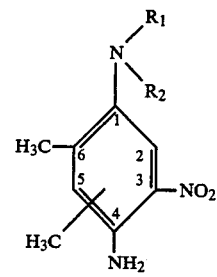

in which $CH_3$ is in position 2 or 5 of the benzene ring and $R_1$ and $R_2$ denote independently of each other a hydrogen atom, a lower alkyl group, a lower mono- or polyhydroxyalkyl or a lower aminoalkyl group in which the amino group is optionally mono- or disubstituted by a lower alkyl radical or by a lower mono- or polyhydroxyalkyl radical, it being understood that the two symbols $R_1$ and $R_2$ can be simultaneously other than hydrogen only when the mobile $CH_3$ radical is in position 5, or cosmetically acceptable salts of these compounds, as well as the process for preparing them and their use in dye compositions, in particular for hair, equally for direct coloring and for coloring by an oxidation route.

15 Claims, No Drawings

NEW DIMETHYL DERIVATIVES OF 3-NITRO-4-AMINOANILINE, PROCESS FOR THEIR PREPARATION AND THEIR USE FOR DYEING KERATINIC FIBERS

The present invention relates to new dimethyl derivatives of 3-nitro-4-aminoaniline, to a process for their preparation and to their use in dyeing keratinic fibres, and in particular human hair.

It is well-known that to give hair a direct colouring, or supplementary sheens in the case of oxidation colouring, use can be made of nitro derivatives of the benzene series. The use of nitroparaphenylenediamines such as more particularly nitroparaphenylenediamine and 2-methyl-5-nitroparaphenylenediamine has already been recommended both for direct dyeing and oxidation dyeing.

However, in recent years, the perfect harmlessness of these nitroparaphenylenediamines has been challenged and, as a result, attempts have been made to replace these colorants in hair-dyeing compositions.

Furthermore, in general, nitroparaphenylenediamines have been found to have poor storage properties in a reducing alkaline medium, in particular including sodium bisulphite, which is usually employed in oxidation dyeing compositions. A search has therefore also been made for nitroparaphenylenediamines having good storage properties in a reducing alkaline medium.

As a result of this research, we have discovered new dimethyl derivatives of 3-nitro-4-aminoaniline having both very low toxicity and a very good stability in solution, particularly when they are employed in an oxidation dyeing composition in the presence of an alkaline agent and a reducer such as sodium bisulphite.

We have also found that hair dyes produced with the aid of these new compounds have a good stability to weathering, light and washing.

A subject of the present invention is therefore new dimethyl derivatives of 3-nitro-4-aminoaniline and a process for preparing them.

The invention is also aimed at dyeing compositions for keratinic fibres, and in particular for human hair, which contain these dimethyl derivatives of 3-nitro-4-amino-aniline, dyeing compositions which can be employed equally well for direct colouring of hair and for colouring by an oxidation route.

Other subjects and benefits of the present invention will become apparent from the reading of the description and the examples which follow.

The dimethyl derivatives of 3-nitro-4-aminoaniline according to the invention correspond to the following formula (1):

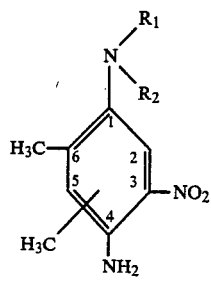

in which the radical $CH_3$ of a variable position can be in position 2 or 5 of the benzene ring and $R_1$ and $R_2$ denote independently of each other a hydrogen atom, a lower alkyl group, lower mono- or polyhydroxyalkyl or lower aminoalkyl the amino group of which may be mono- or disubstituted, if appropriate, by a lower alkyl radical or a lower mono- or polyhydroxyalkyl radical, it being understood that the two symbols $R_1$ and $R_2$ may simultaneously be other than hydrogen only when the mobile $CH_3$ radical is in position 5.

These derivatives of formula (I) can also exist in the form of cosmetically acceptable salts.

According to the invention, the lower alkyl group is an alkyl group containing 1 to 6 carbon atoms and preferably 1 to 4 carbon atoms.

Particularly preferred radicals $R_1$ and $R_2$ according to the invention are the methyl, ethyl, n-propyl, β-hydroxyethyl, β-hydroxypropyl, γ-hydroxypropyl, β,γ-dihydroxypropyl, β-aminoethyl, γ-aminopropyl and β-N,N-diethylaminoethyl radicals. Preferred compounds are those in which at least one of the radicals $R_1$ and $R_2$ denotes a hydrogen atom.

Compounds which are particularly harmless and resistant to washing and to light are the following compounds:

2,6-dimethyl-3-nitroparaphenylenediamine
5,6-dimethyl-3-nitroparaphenylenediamine
4-amino-2,6-dimethyl-3-nitro-N-methylaniline
4-amino-5,6-dimethyl-3-nitro-N-β-hydroxyethylaniline
4-amino-5,6-dimethyl-3-nitro-N-β,γ-dihydroxypropylaniline
4-amino-5,6-dimethyl-3-nitro-N-β-aminoethylaniline, and
4-amino-5,6-dimethyl-3-nitro-N-(β-diethylaminoethyl)aniline.

2,5-Dimethyl-3-nitroparaphenylenediamine which is also synthesised has colouring properties but does not have the considerable advantages of the preferred compounds. Their useful properties appear to be due, without this interpretation being of a limiting nature, to the presence of a methyl radical in para position relative to the $NO_2$ group.

The compounds of formula (I) in which $R_1$ and $R_2$ both denote hydrogen can be prepared by nitration of the compounds of the following formula (II):

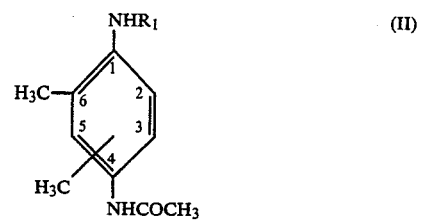

in which $R_1$ denotes a hydrogen atom when $CH_3$ is in position 2 and $R_1$ denotes the acetyl group (—$COCH_3$) when $CH_3$ is in position 5.

When the radical —$CH_3$ is in position 5 with $R_1$ denoting —$COCH_3$, the substance in question is the N,N'-diacetyl derivative of 5,6-dimethylparaphenylenediamine, which is a known compound.

When the radical $CH_3$ is in position 2, $R_1$ denoting hydrogen, the substance is 2,6-dimethyl-4-acetylaminoaniline, which is a new compound obtained by controlled acetylation in water, at ambient temperature, in the presence of sodium sulphite, of 2,6-dimethylparaphenylenediamine dihydrochloride.

Nitration of the compounds II is carried out in a conventional manner. The compounds II, after being dissolved at ambient temperature in 96% sulphuric acid, are treated between −5° and 0° C. with a sulphonitric mixture, resulting in the compounds of the following formula III:

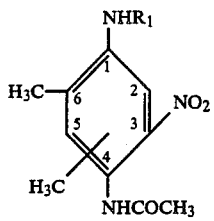
(III)

in which $R_1$ has the same meanings as in formula (II) above and $CH_3$ the same positions as those indicated above.

The compounds of formula (III) obtained in this way are then hydrolysed with the aid of hydrochloric acid.

The compounds of formula (I) in which at least one of the symbols $R_1$ and $R_2$ is other than hydrogen are prepared according to the following two procedures, according to whether they are derivatives of 2,6-dimethyl-3-nitroparaphenylenediamine or derivatives of 5,6-dimethyl-3-nitroparaphenylenediamine.

1. Preparation of the secondary amines derived from 2,6-dimethyl-3-nitroparaphenylenediamine In this case it is necessary to carry out the alkylation of the amine in position 1 on a precursor which is the p-toluenesulphonamide of 2,6-dimethyl-4-nitroaniline. Alkylating agents which may be mentioned by way of non-limiting examples are alkyl sulphates or alkyl halides, substituted or unsubstituted. After desulphonation by hydrolysis, the alkylated 4-nitroaniline is reduced to a substituted 2,6-dimethylparaphenylenediamine, which is finally nitrated after acetylation of the primary amine, and then hydrolysed.

The reaction scheme is the following:

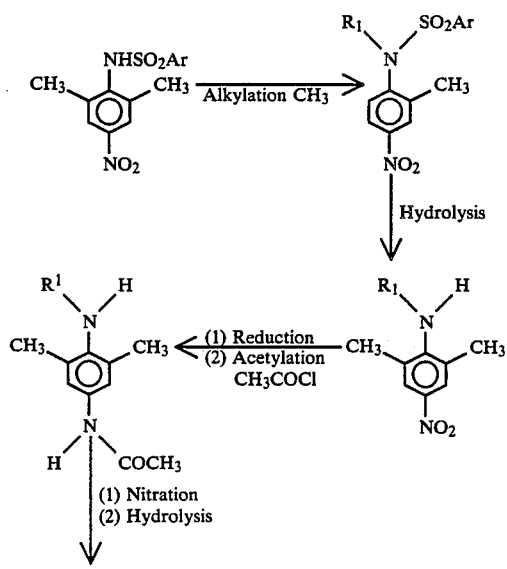

-continued

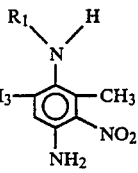

Ar denoting the p-tolyl group and $R_1$ having the meanings shown for formula (I), except for hydrogen.

2. Preparation of the secondary and tertiary amines derived from 5,6-dimethyl-3-nitroparaphenylenediamine In this case, the substitution of the amine in position 1, the amine being more reactive, can be carried out directly, starting from 5,6-dimethyl-3-nitroparaphenylenediamine, by alkylation with the aid of an alkyl halide, substituted or unsubstituted, an epoxide or by the opening of a 1,3-oxazolin-2-one intermediate.

The dyeing compositions according to the invention contain, in a solvent medium, at least one compound corresponding to the formula (I) and may be employed for direct colouring of keratinic fibres or for oxidation colouring of these fibres, in which case the compounds of formula (I) impart supplementary sheens to the base colouring obtained by oxidising development of precursors of oxidation colorants.

These compositions incorporate the compounds according to the invention in proportions of between 0.001 and 5% by weight and preferably between 0.05 and 2% by weight relative to the total weight of the composition.

The solvent medium is preferably a cosmetic vehicle generally consisting of water, but it is also possible to add to the compositions organic solvents, to dissolve compounds which might be inadequately soluble in water. Among these solvents, mention can be made of the lower alkanols such as ethanol and isopropanol, aromatic alcohols such as benzyl alcohol, polyols such as glycerol, glycols or glycol ethers such as 2-butoxyethanol or 2-ethoxyethanol, ethylene glycol, propylene glycol, diethylene glycol monoethyl ether and diethylene glycol monomethyl ether, as well as analogous products and their mixtures. These solvents are preferably present in proportions ranging from 1 to 75% by weight and, in particular, from 5 to 50% by weight relative to the total weight of the composition.

These compositions may incorporate anionic, cationic, nonionic or amphoteric surface-active agents or their mixtures. These surface-active products are present in the compositions of the invention in proportions of between 0.5 and 55% by weight and preferably between 4 and 40% by weight relative to the total weight of the composition.

The compositions may be thickened preferably with compounds chosen from sodium alginate, gum arabic, cellulose derivatives such as methyl cellulose, hydroxyethyl cellulose, hydroxypropylmethyl cellulose, carboxymethyl cellulose and various polymers which act as thickeners, such as more particularly acrylic acid derivatives. It is also possible to employ inorganic thickening agents such as bentonite. These thickening agents are present preferably in proportions of between 0.5 and 10% by weight and particularly between 0.5 and 3% by weight relative to the total weight of the composition.

The compositions according to the invention may also contain various adjuvants usually employed in hair-dyeing compositions and in particular penetrating agents, dispersing agents, sequestering agents, film-forming agents, buffers and perfumes.

These compositions may take various forms such as liquid, cream, gel or any other suitable form to produce a hair dye. They may, moreover, be packaged in aerosol bottles in the presence of a propellant.

The pH of these dyeing compositions may be between 3 and 11.5, preferably between 5 and 11.5. It is adjusted to the required value with the aid of an alkalising agent such as aqueous ammonia, sodium carbonate, potassium carbonate or ammonium carbonate, sodium hydroxide or potassium hydroxide, alkanolamines such as mono-, di- or triethanolamine, 2-amino-2-methylpropan-1-ol, 2-amino-2-methylpropane-1,3-diol, alkylamines such as ethylamine or triethylamine, or with the aid of an acidifying agent such as phosphoric, hydrochloric, tartaric, acetic, lactic or citric acid.

When the compositions are intended to be employed in a process for direct hair colouring, they may contain, in addition to the compounds according to the invention, other direct colorants such as azo or anthraquinone colorants, such as for example 1,4,5,8-tetraaminoanthraquinone, nitro colorants of the benzene series other than the compounds of formula (I) and more particularly the following compounds:

2-methyl-6-nitroaniline,
2-methyl-4-amino-5-nitrophenol,
3-nitro-4-N'-$\beta$-hydroxyethylamino-N-methylaniline,
3-nitro-4-N'-$\beta$-hydroxyethylamino-N-methyl-N-$\beta$-hydroxyethylaniline,
4-amino-3-nitrophenol,
3-amino-4-nitrophenol,
2-amino-3-nitrophenol,
2-N-$\beta$-hydroxyethylamino-5-nitrophenol,
2-N-hydroxyethylamino-5-nitroanisole,
2-methyl-5-nitro-N,N'-($\beta$-hydroxyethyl)paraphenylenediamine,
3-nitro-4-N'-($\beta$-hydroxyethyl)amino-N,N'di($\beta$-hydroxyethyl)aniline,
3-nitro-4-N'-($\beta$-aminoethyl)amino-N,N-di($\beta$-hydroxyethyl)aniline,
4-amino-2-methyl-3-nitro-N-$\beta$-hydroxyethylaniline,
(4-N-hydroxyethylamino-3-nitro)phenyl, $\beta$-hydroxyethyl ether,
(3-N-methylamino-4-nitro)phenyl, $\beta$-hydroxyethyl ether, or
2-isopropyl-6-nitroaniline, employed in free form or in the form of their salts.

The concentration of these direct colorants other than the colorants of formula (I) may be between 0.001 and 5% by weight relative to the total weight of the composition.

These compositions, employed in a process for dyeing by direct colouring, are applied to the keratinic fibres for an application period which varies from 5 to 50 minutes, then the fibres are rinsed, washed if appropriate, rinsed again and dried.

The compositions according to the invention may also be employed in the form of hair setting lotions intended to impart a slight colouring to the hair and to improve the setting behaviour at the same time. In this case, they are in the form of aqueous, alcoholic or aqueous-alcohol solutions containing at least one cosmetic resin and they are applied to damp, previously washed and rinsed, hair which may be wound and then dried.

The cosmetic resins employed in the hair setting lotions may in particular be polyvinylpyrrolidone, copolymers of crotonic acid with vinyl acetate, vinylpyrrolidone with vinyl acetate, maleic anhydride with butyl vinyl ether, maleic anhydride with methyl vinyl ether, as well as any other cationic, anionic, nonionic or amphoteric polymer usually employed in this type of composition. These cosmetic resins are present in the compositions of the invention in a concentration of 0.5 to 4% by weight, and preferably from 1 to 3% by weight based on the total weight of the composition.

When the compositions according to the invention form oxidation dyeings which involve development with an oxidant, the compounds of formula (I) according to the invention are employed essentially with a view to introducing sheens in the final dye.

These compositions then contain precursors of oxidation colorants in combination with at least one nitro colorant of formula (I) and optionally other nitro colorants such as those mentioned above.

They may contain, for example, paraphenylenediamines such as: paraphenylenediamine, paratolylenediamine, 2-chloroparaphenylenediamine, 2,6-dimethylparaphenylenediamine, 2,6-dimethyl-3-methoxyparaphenylenediamine, N-($\beta$-methoxyethyl)paraphenylenediamine, N,N-($\beta$-hydroxyethyl)paraphenylenediamine, 4-N,N-(ethyl, carbamylmethyl)aminoaniline, as well as their salts.

They may also contain paraaminophenols, for example: paraaminophenol, N-methyl paraaminophenyl, 2-chloro-4-aminophenol, 3-chloro-4-aminophenol, 2-methyl-4-aminophenol, and their salts.

They may also contain orthoaminophenol.

They may also contain heterocyclic derivatives, for example 2,5-diaminopyridine, or 7-aminobenzomorpholine.

The compositions according to the invention may contain, in combination with the precursors of oxidation colorants, couplers which are well-known in the state of the art.

As couplers, there may be mentioned in particular: metadiphenols such as resorcinol, 2-methylresorcinol, metaaminophenols such as metaaminophenol, 2-methyl-5-aminophenol, 2-methyl-5-N-methylaminophenol, 2-methyl-5-N-($\beta$-hydroxyethyl)aminophenol, and their salts, metaphenylenediamines such as: 2,4-diaminophenoxyethanol, (2-N-$\beta$-hydroxyethylamino-4-amino)-phenoxyethanol, 2,4-diaminophenyl$\beta$,$\gamma$-dihydroxypropyl ether and their salts, metaacylaminophenols, metaureidophenols, metacarbalkoxyaminophenols such as: 2-methyl-5-acetylaminophenol, 2-methyl-5-ureidophenol, and 2-methyl-5-carbethoxyaminophenol.

Finally, mention can be made, as other couplers which can be employed in the compositions of the invention, of $\alpha$-naphthol, couplers containing an active methylene group such as the diketo compounds and pyrazolones and heterocyclic couplers such as 2,4-diaminopyridine, 6-hydroxybenzomorpholine, 6-aminobenzomorpholine, as well as their salts.

In addition to the precursors of oxidation colorants, these compositions contain reducing agents such as more particularly sodium bisulphite, sodium sulphite, thioglycolic acid, thiolactic acid, mercaptosuccinic acid, ascorbic acid and their salts and hydroquinone. These reducing agents are present in proportions of between 0.05 and 3% by weight relative to the total weight of the composition.

The precursors of oxidation colorants may be employed in the compositions of the invention at concentrations of between 0.001 and 5% by weight and preferably between 0.03 and 2% by weight based on the total weight of the composition. The couplers may also be present in proportions of between 0.001 and 5% by weight, preferably between 0.015 and 2% by weight. The pH of these compositions for oxidation dyeing is preferably between 7 and 11.5 and is adjusted with the aid of the alkalising agents defined above.

We have found that the compounds according to the invention were particularly stable in such compositions.

The process for dyeing keratinic fibres, in particular human hair, making use of development with an oxidant, consists in applying to hair the dye composition incorporating both a colorant according to the invention and precursors of colorants. The development of the colouring can then take place slowly in the presence of atmospheric oxygen, but preferably a chemical developing system is employed which is most frequently chosen from hydrogen peroxide, urea peroxide and per-salts. In particular, a 20-volume hydrogen peroxide solution is employed.

Once the composition with the oxidising agent has been applied to the keratinic fibres, it is left in place for 10 to 50 minutes, preferably 15 to 30 minutes, after which the keratinic fibres are rinsed, washed, if appropriate, with shampoo, rinsed again and dried.

The examples which follow are intended to illustrate the invention without being of a limiting nature.

PREPARATIVE EXAMPLE 1

Preparation of 2,6-dimethyl-3-nitroparaphenylenediamine

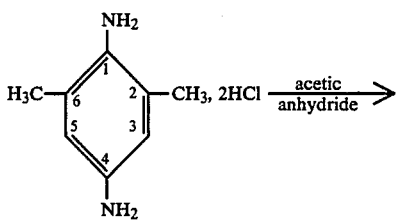

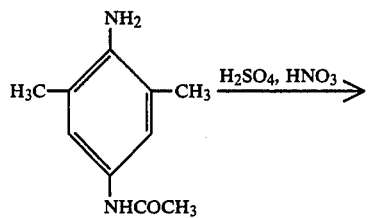

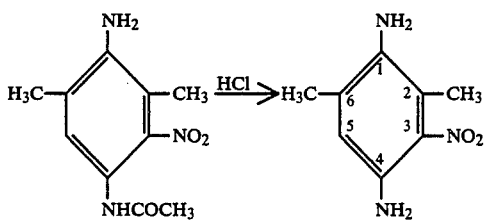

First stage

Preparation of 2,6-dimethyl-4-acetylaminoaniline 1.6 moles (334.6 g) of 2,6-dimethylparaphenylenediamine dihydrochloride are dissolved in 1600 ml of water. To this solution are added 3.36 moles (423.3 g) of sodium sulphite dissolved in 1600 ml of water and then, in small proportions, with stirring, keeping the temperature in the region of 25° C., 1.68 moles (174.8 g) of acetic anhydride. When the addition is complete the reaction mixture is left for one hour at ambient temperature. After cooling, the monoacetyl derivative which has precipitated is filtered off. It melts at 148° C.

Second stage

Preparation of 2,6-dimethyl-3-nitro-4-acetylaminoaniline 0.226 mole (40.3 g) of the monoacetyl derivative obtained earlier is added in small portions, with good stirring, to 230 ml of 96% sulphuric acid, while the temperature is maintained between 18° and 20° C. The dissolution is complete after 30 minutes. This solution is then cooled to $-3°$ C. and then the sulphonitric mixture prepared from 10.5 ml of nitric acid (d=1.5) and 40 ml of 96% sulphuric acid is added to it dropwise over 45 minutes, with good stirring and while the temperature is maintained between $-2°$ and $0°$ C. When the addition is complete, the reaction mixture is kept for one hour at 0° C. and is then poured on 2 kg of crushed ice. After neutralisation with aqueous ammonia, the expected product which has precipitated is filtered off, washed with water and recrystallised from ethanol. It melts at 197° C.

| | Analysis | |
|---|---|---|
| | Calculated for $C_{10}H_{13}N_3O_3$ | Found |
| C % | 53.80 | 53.83 |
| H % | 5.87 | 5.92 |
| N % | 18.83 | 18.93 |
| O % | 21.50 | 21.35 |

Third stage

Preparation of 2,6-dimethyl-3-nitroparaphenylenediamine 0.04 mole (8.9 g) of 2,6-dimethyl-3-nitro-4-acetylaminoaniline, to which 10 ml of acetic acid have been added, are added to 25 ml of 36% hydrochloric acid. After one and a half hours' heating on a boiling water bath, the expected product is filtered off in the form of hydrochloride. This hydrochloride is dissolved in 40 ml of water. 2,6-Dimethyl-3-nitroparaphenylenediamine is precipitated by adding aqueous ammonia. The product is filtered off, washed with water, dried and recrystallised from benzene. It melts at 124° C.

| | Analysis | |
|---|---|---|
| | Calculated for $C_8H_{11}N_3O_2$ | Found |
| C % | 53.03 | 53.23 |
| H % | 6.12 | 6.14 |
| N % | 23.19 | 23.22 |
| O % | 17.66 | 17.58 |

PREPARATIVE EXAMPLE 2

Preparation of 5,6-dimethyl-3-nitroparaphenylenediamine

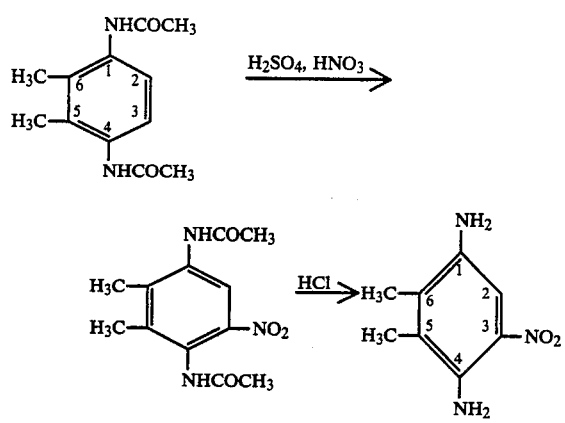

First stage

Preparation of 5,6-dimethyl-3-nitro-N,N'-diacetylparaphenylenediamine 0.085 mole (18.3 g) of 5,6-dimethyl-N-N'-diacetyl-paraphenylenediamine is added in small portions, with good stirring, to 85 ml of 96% sulphuric acid, while the temperature is maintained between 18° and 20° C. The dissolution is complete after 30 minutes. This solution is cooled to −5° C. and the sulphonitric mixture prepared in accordance with the usual process, from 15 ml of 96% sulphuric acid and 4 ml of nitric acid (d=1.5) is then added to it dropwise over 20 minutes, while the temperature is maintained in the region of −2° C. When the addition is complete, stirring is continued for 1 hour in the region of 0° C., and then the reaction mixture is poured on 0.8 kg of crushed ice. The expected product which has precipitated is filtered off, washed with water and dried under vacuum at 50° C. After recrystallisation from ethanol it melts above 260° C.

| Analysis | Calculated for $C_{12}H_{15}N_3O_4$ | Found |
|---|---|---|
| C % | 54.33 | 54.36 |
| H % | 5.70 | 5.70 |
| N % | 15.84 | 15.93 |
| O % | 24.13 | 24.30 |

Second stage

Preparation of 5,6-dimethyl-3-nitroparaphenylenediamine 0.075 mole (19.9 g) of the diacetyl derivative prepared according to the process of the first stage is heated for one and a half hours on a boiling water bath, in 75 ml of 36% hydrochloric acid.

After the mixture has cooled the expected product in the form of hydrochloride is filtered off. This hydrochloride is dissolved in 150 ml of water and made alkaline with aqueous ammonia to precipitate 5,6-dimethyl-3-nitroparaphenylenediamine. The product is filtered off, washed with water, and recrystallized with the aid of ethyl acetate; it melts at 159° C.

| Analysis | Calculated for $C_8H_{11}N_3O_2$ | Found |
|---|---|---|
| C % | 53.03 | 52.96 |
| H % | 6.12 | 6.08 |
| N % | 23.19 | 23.14 |
| O % | 17.66 | 17.71 |

PREPARATIVE EXAMPLE 3

Preparation of 4-amino-2,6-dimethyl-3-nitro-N-methylaniline

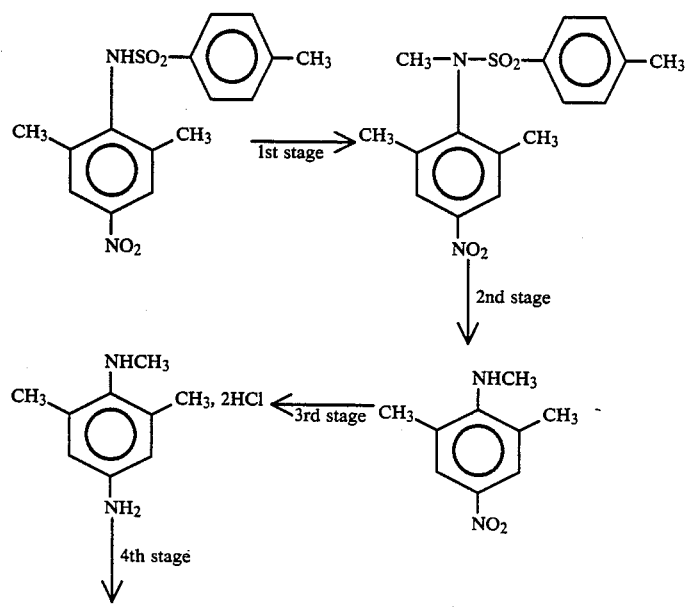

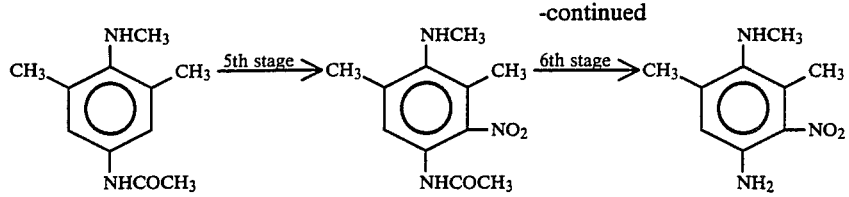

First stage

Preparation of 1-N,N(methyl, p-toluenesulphonyl-)amino-2,6-dimethyl-4-nitrobenzene 0.053 mole (16.9 g) of 1-p-toluenesulphonylamino-2,6-dimethyl-4-nitrobenzene, prepared according to BM WEPSTER, Recueil Tr. Chimiques, Pays-Bas, 73, 809 (1954), is dissolved in 120 ml of N/2 caustic soda. 0.06 mole (6 g) of dimethyl sulphate is added in small portions at 20° C. Stirring is continued for 1 hour.

After the precipitate has been filtered off and made into a paste with water, a product is obtained which recrystallises from ethanol and melts at 128° C.

Analysis of the product obtained gives the following results:

|   | Analysis % Calculated for $C_{16}H_{18}N_2O_4S$ | % Found |
|---|---|---|
| C | 57.48 | 57.41 |
| H | 5.43  | 5.35  |
| N | 8.38  | 8.29  |
| O | 19.15 | 19.31 |
| S | 9.57  | 9.58  |

Second stage

Preparation of 2,6-dimethyl-4-nitro-N-methylaniline 0.031 mole (10.4 g) of 1-N,N-(methyl, p-toluenesulphonyl)amino-2,6-dimethyl-4-nitrobenzene is added in small portions to a solution of 25 ml of 96% sulphuric acid and 2.5 ml of water, which has been heated to 60° C. After 30 minutes' additional heating, the reaction mixture is poured on 90 g of ice. The sulphate of the expected product is filtered off.

The sulphate is suspended in water and then 20% aqueous ammonia is added; the expected product crystallises. After recrystallisation from 96° alcohol, it melts at 99° C.

Analysis of the product obtained gives the following results:

|   | Analysis % Calculated for $C_9H_{12}N_2O_2$ | % Found |
|---|---|---|
| C | 59.98 | 60.06 |
| H | 6.71  | 6.75  |
| N | 15.55 | 15.50 |
| O | 17.76 | 17.77 |

Third stage

Preparation of 4-amino-2,6-dimethyl-N-methylaniline dihydrochloride

A suspension of 15.5 g of powdered zinc and 0.6 g of ammonium chloride is heated to reflux. After the source of heat has been removed, 0.02 mole (3.6 g) of 2,6-dimethyl-4-nitro-N-methylaniline is added so as to maintain reflux. At the end of the addition, the reaction mixture is filtered boiling into a solution of 0.05 mole of hydrochloric acid in 14 ml of absolute ethanol; the dihydrochloride crystallises from the filtrate. After recrystallisation from an alcohol-water mixture, a white product is obtained:

molecular weight calculated for $C_9H_{16}N_2Cl_2$: 223
molecular weight determined by aqueous potentiometric titration using caustic soda: 220.

Analysis of the product obtained gives the following results:

|   | Analysis % Calculated for $C_9H_{16}N_2Cl_2$ | % Found |
|---|---|---|
| C  | 48.44 | 48.51 |
| H  | 7.23  | 7.28  |
| N  | 12.55 | 12.47 |
| Cl | 31.78 | 31.77 |

Fourth stage

Preparation of 4-N-methylamino-3,5-dimethylacetanilide 0.37 mole (46.6 g) of sodium sulphite dissolved in 170 ml of water are added in one portion to a solution of 0.17 mole (38 g) of 4-amino-2,6-dimethyl-N-methylaniline dihydrochloride in 170 ml of water, followed by dropwise addition over 30 minutes of 0.183 mole (19 g) of acetic anhydride, the temperature being maintained between 18° and 23° C. After 2 hours of stirring, the material is filtered and the filtrate neutralised with 20% strength aqueous ammonia. After filtering off, washing with water and drying under vacuum, 0.12 mole (23.3 g) of the expected product is obtained; it melts at 82° C.

Molecular weight calculated for $C_{11}H_{16}N_2O$: 192.3
Molecular weight determined by potientiometric titration in acetic acid using perchloric acid: 195.

Fifth stage

Preparation of 4-N-methylamino-3,5-dimethyl-2-nitroacetanilide

A solution of 5.6 ml of nitric acid (d=1.50) in 20 ml of concentrated sulphuric acid is added in small portions to 0.12 mole (23 g) of 4-N-methylamino-3,5-dimethylacetanilide in 120 ml of concentrated sulphuric acid while the temperature is maintained at 0° C. After 30 minutes of additional stirring the reaction mixture is poured on 1 kg of ice. After being neutralised with 20% strength aqueous ammonia, the expected product precipitates. Filtered off and recrystallised from 96° alcohol, it melts at 133° C.

Molecular weight calculated for $C_{11}H_{15}N_3O_3$: 237
Molecular weight found by potentiometric titration with perchloric acid in acetic acid: 240.

Analysis of the product obtained gives the following results:

| Analysis | | |
|---|---|---|
| % Calculated for $C_{11}H_{15}N_3O_3$ | | % Found |
| C | 55.68 | 55.55 |
| H | 6.37 | 6.40 |
| N | 17.71 | 17.80 |
| O | 20.23 | 20.00 |

Sixth stage

Preparation of 4-amino-2,6-dimethyl-3-nitro-N-methylaniline 0.11 mole (26.0 g) of 4-N-methylamino-3,5-dimethyl-2-nitroacetanilide is added to 65 ml of concentrated hydrochloric acid. The mixture is heated for 1 hour at 95° C. After cooling, the dihydrochloride of the expected product is filtered off.

The dihydrochloride obtained in this way is suspended in 400 ml of water. The mixture is neutralised with 20% strength aqueous ammonia, the expected product crystallises. After being filtered off and dried under vacuum in the presence of phosphorus pentoxide, it is recrystallised from a mixture of cyclohexane and benzene; it melts at 57° C.

Molecular weight calculated for $C_9H_{13}N_3O_2$: 195
Molecular weight found by potentiometric titration in acetic acid using perchloric acid: 195.

Analysis of the product obtained gives the following results:

| Analysis | | |
|---|---|---|
| % Calculated for $C_9H_{13}N_3O_2$ | | % Found |
| C | 55.37 | 55.43 |
| H | 6.71 | 6.69 |
| N | 21.53 | 21.54 |
| O | 16.39 | 16.41 |

PREPARATIVE EXAMPLE 4

Preparation of 4-amino-5,6-dimethyl-3-nitro-N-β-hydroxyethylaniline

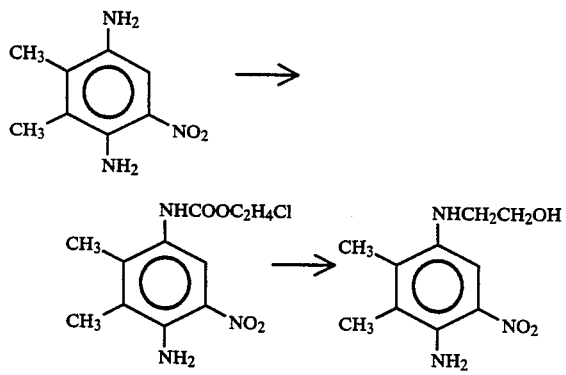

First stage

Preparation of β-chloroethyl 4-amino-5,6-dimethyl-3-nitrophenylcarbamate 0.05 mole (9.1 g) of 5,6-dimethyl-3-nitroparaphenylenediamine is dissolved in 40 ml of dioxane. 0.055 mole (5.5 g) of calcium carbonate is added. The temperature is raised to 90° C. and then 0.053 mole (7.6 g) of β-chloroethyl chloroformate is added in small portions with stirring. After the end of the addition heating is continued for 1 hour. The reaction mixture is poured into 200 g of iced water. The expected product precipitates. After being filtered off, made into a paste with water and recrystallised from 96° ethanol, it melts at 151° C.

Analysis of the product obtained gives the following results:

| Analysis | | |
|---|---|---|
| % Calculated for $C_{11}H_{14}N_3O_4Cl$ | | % Found |
| C | 45.92 | 46.10 |
| H | 4.90 | 4.89 |
| N | 14.61 | 14.50 |
| O | 22.24 | 22.25 |

Second stage

Preparation of 4-amino-5,6-dimethyl-3-nitro-N-β-hydroxyethylaniline 0.0417 mole (12 g) of β-chloroethyl 4-amino-5,6-dimethyl-3-nitrophenylcarbamate is suspended in 36 ml of 96° alcohol. A solution of 6.2 g of caustic soda pellets of 97% strength in 15 ml of water is added in small portions with stirring; the reaction mixture is heated to the refluxing temperature of the alcohol. After being heated for 2 hours the reaction mixture is poured into 200 g of iced water and acidified with acetic acid.

After being filtered off, made into a paste with water and recrystallised from ethylacetate, the product melts at 166° C.

Molecular weight calculated for $C_{10}H_{15}N_3O_3$: 225.25
Molecular weight found by potentiometric titration in acetic acid using perchloric acid: 223.

Analysis of the product obtained gives the following results:

| Analysis | | |
|---|---|---|
| % Calculated for $C_{10}H_{15}N_3O_3$ | | % Found |
| C | 53.32 | 53.27 |
| H | 6.71 | 6.77 |
| N | 18.66 | 18.76 |
| O | 21.31 | 21.25 |

PREPARATIVE EXAMPLE 5

Preparation of 4-amino-5,6-dimethyl-3-nitro-N-β,β-dihydroxypropylaniline

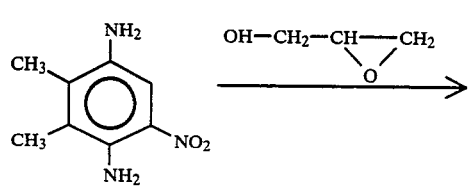

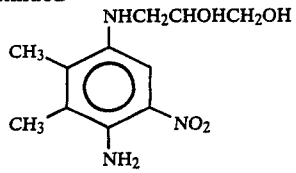

0.05 mole (9 g) of 5,6-dimethyl-3-nitroparaphenylenediamine and 0.1 mole (7.4 g) of glycidol in 18 ml of ethanol are heated on a boiling water bath with stirring.

After being heated for 2 hours the reaction mixture is cooled, the precipitate is filtered off, washed with water and with alcohol and then dried. After being dissolved in dimethyl sulphoxide and then reprecipitated by adding water, and dried, it melts at 181° C.

Analysis of the product obtained gives the following results:

| | Analysis | |
|---|---|---|
| | % Calculated for $C_{11}H_{17}N_3O_4$ | % Found |
| C | 51.76 | 51.77 |
| H | 6.67 | 6.70 |
| N | 16.47 | 16.34 |
| O | 25.10 | 24.91 |

PREPARATIVE EXAMPLE 6

Preparation of 4-amino-5,6-dimethyl-3-nitro-N-β-aminoethylaniline

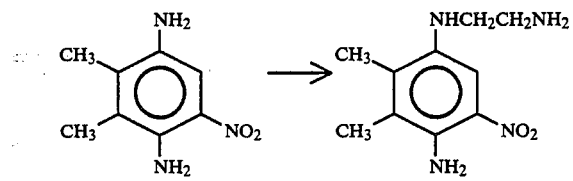

A suspension of 0.5 mole (90 g) of 5,6-dimethyl-3-nitroparaphenylenediamine and of 0.75 mole (75 g) of calcium carbonate in 350 ml of water and 150 ml of 96° alcohol is first heated to 80° C. with stirring. 1.2 moles (252 g) of bromoethylamine hydrobromide are added in small portions with stirring. After being heated under reflux for one and a half hours the reaction mixture is cooled and 250 ml of concentrated hydrochloric acid are run into it; the precipitate obtained in this way is filtered off, washed with water and then with acetone. After it has been dissolved in 1 liter of iced water by adding aqueous ammonia the salt of the expected product is obtained which, after being made alkaline with 250 ml of 10N caustic soda, yields 4-amino-5,6-dimethyl-3-nitro-N-β-aminoethylaniline. After being washed with water, dried and recrystallised from ethyl alcohol, the product melts at 152° C.

| | Analysis | |
|---|---|---|
| | % Calculated for $C_{10}H_{16}N_4O_2$ | % Found |
| C | 53.57 | 53.62 |
| H | 7.14 | 7.18 |
| N | 25.00 | 24.91 |
| O | 14.29 | 14.12 |

PREPARATIVE EXAMPLE 7

Preparation of 4-amino-5,6-dimethyl-3-nitro-N-β-diethylaminoethylaniline

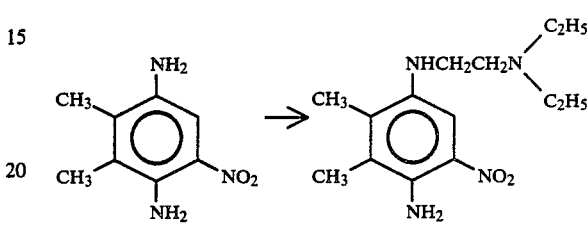

A mixture consisting of 0.05 mole (9 g) of 5,6-dimethyl-3-nitroparaphenylenediamine, 0.075 mole (7.5 g) of calcium carbonate and 0.1 mole (17.2 g) of 1-bromo-2-N,N-diethylaminoethane hydrochloride in 36 ml of water and 18 ml of 96° ethanol is heated to 80° C. with stirring. After 45 minutes' heating the reaction mixture is filtered hot and 25 ml of hydrochloric acid are added to the filtrate. The hydrochloride of the expected product precipitates. It is filtered off and washed with acetone.

The hydrochloride is dissolved in water and an oil, which precipitates, is obtained by adding 10N caustic soda in the presence of ice. After being filtered off, washed with water and dried under vacuum in the presence of phosphorus pentoxide, the product obtained is recrystallised from 96° ethanol. It melts at 98° C.

Analysis of the product obtained gives the following results:

| | Analysis | |
|---|---|---|
| | % Calculated for $C_{14}H_{24}N_4O_2$ | % Found |
| C | 60.00 | 59.96 |
| H | 8.57 | 8.46 |
| N | 20.00 | 20.02 |
| O | 11.43 | 11.67 |

EXAMPLE 1

Direct dyeing

The following dye composition is prepared:

| | |
|---|---|
| 4-amino-2,6-dimethyl-3-nitro-N—methylaniline | 0.3 g |
| 4-amino-2-methyl-3-nitro-N—β-hydroxyethylaniline | 0.12 g |
| 3-nitro-4-N'—β-aminoethylamino-N,N—β-hydroxyethylaniline dihydrochloride | 0.18 g |
| 2-amino-3-nitrophenol | 0.12 g |
| propylene glycol | 10 g |
| hydroxyethylcellulose sold under the name CELLOSIZE W.P.03 by UNION CARBIDE | 2 g |
| cetyldimethylhydroxyethylammonium chloride sold under the name CHIMEXON by the Company CHIMEX | 2 g |
| 5% strength aqueous ammonia | 4 ml |
| water q.s. | 100 g |

-continued

| | |
|---|---|
| pH | 9.2 |

This mixture, applied for 20 minutes at 28° C. to permanent-waved, 90% naturally white hair, gives it, after shampooing and rinsing, a mahogany colour.

EXAMPLE 2

Direct dyeing

The following dye composition is prepared:

| | |
|---|---|
| 4-amino-2,6-dimethyl-3-nitro-N—methylaniline | 0.055 g |
| 96° alcohol | 10 g |
| ALFOL C16/18 E | 8 g |
| (cetylstearyl alcohol sold by the Company CONDEA) | |
| Cire de Lanette E | 0.5 g |
| (sodium cetylstearyl sulphate sold by HENKEL) | |
| CEMULSOL B | 1 g |
| (ethoxylated castor oil sold by RHONE-POULENC) | |
| oleyl diethanolamide | 1.5 g |
| 5% strength aqueous ammonia | 1 g |
| water q.s. | 100 g |
| pH | 9.8. |

This mixture, applied for 30 minutes at 28° C. to white-bleached hair, gives it, after shampooing and rinsing, a light golden yellow colour.

EXAMPLE 3

Direct dyeing

The following dye composition is prepared:

| | |
|---|---|
| 4-amino-5,6-dimethyl-3-nitro-N—β-hydroxyethyl-aniline | 0.385 g |
| 2-N—β-hydroxyethylamino-5-nitrophenol | 0.085 g |
| 3-nitro-4-N'—β-hydroxyethylamino-N—methyl-N—β-hydroxyethylaniline | 0.15 g |
| 2-butoxyethanol | 10 g |
| ALFOL C16/18 E | 8 g |
| (cetylstearyl alcohol sold by the Company CONDEA) | |
| Cire de Lanette E | 0.5 g |
| (sodium cetylstearyl sulphate sold by HENKEL) | |
| CEMULSOL B | 1 g |
| (ethoxylated castor oil sold by RHONE-POULENC) | |
| oleyl diethanolamide | 1.5 g |
| 1% strength triethanolamine solution | 2 ml |
| water q.s. | 100 g |
| pH | 7.6. |

This mixture, applied for 25 minutes at 28° C. to white-bleached hair, gives it, after shampooing and rinsing, a light copper colour.

EXAMPLE 4

Direct dyeing

The following dye composition is prepared:

| | |
|---|---|
| 4-amino-5,6-dimethyl-3-nitro-N—β-hydroxyethyl-aniline | 2 g |
| 2-butoxyethanol | 25 g |
| CARBOPOL 934 from GOODRICH CHEMICAL Co. | 2 g |
| (acrylic acid polymer, MW: 2 to 3 million) | |
| pure triethanolamine | 4.5 g |
| water q.s. | 100 g |
| pH | 7.6. |

This mixture, applied for 15 minutes at 30° C. to 90% naturally white hair, gives it, after shampooing and rinsing, a pink beige colour.

EXAMPLE 5

Direct dyeing

The following dye mixture is prepared:

| | |
|---|---|
| 4-amino-5,6-dimethyl-3-nitro-N—β, γ-dihydroxy-propylaniline | 0.25 g |
| 2-butoxyethanol | 6 g |
| LAURAMIDE - WITCO Company | 1.5 g |
| (lauric acid monoethanolamide) | |
| lauric acid | 1 g |
| CELLOSIZE W.P.03 - UNION CARBIDE Company | 5 g |
| (hydroxyethylcellulose) | |
| monoethanolamine | 2 g |
| water q.s | 100 g |
| pH | 9.3. |

This mixture, applied for 20 minutes at 28° C. to white-bleached hair, gives it, after shampooing and rinsing, a colour of 2.5 R 8/6 according to the Munsell notation.

EXAMPLE 6

Direct dyeing

The following dye mixture is prepared:

| | |
|---|---|
| 4-amino-5,6-dimethyl-3-nitro-N—β,γ-dihydroxypropyl-aniline | 0.2 g |
| 4-N'—β-hydroxyethylamino-3-nitro-N,N—di(β-hydroxyethyl)-aniline hydrochloride | 0.50 g |
| 4-amino-3-nitrophenol | 0.1 g |
| 2-butoxyethanol | 10 g |
| ALFOL $C_{16/18E}$-CONDEA Company | 8 g |
| (cetylstearyl alcohol) | |
| Cire de Lanette E - HENKEL Company | 0.5 g |
| (sodium cetylstearyl sulphate) | |
| CEMULSOL B - RHONE-POULENC Company | 1 g |
| (ethoxylated castor oil) | |
| oleyl diethanolamide | 1.5 g |
| water q.s | 100 g |
| pH | 7.2. |

This mixture, applied for 20 minutes at 30° C. to 90% naturally white hair, gives it, after shampooing and rinsing, a golden honey colour.

EXAMPLE 7

Direct dyeing

The following dye mixture is prepared:

| | |
|---|---|
| 4-amino-5,6-dimethyl-3-nitro-N—β-aminoethyl-aniline | 0.5 g |
| 96° ethyl alcohol | 10 g |
| COMPERLAN KD - HENKEL Company | 2.2 g |
| (copra fatty acid diethanolamide) | |
| lauric acid | 0.8 g |
| ethylene glycol monoethyl ether | 2 g |
| monoethanolamine | 6 g |
| water q.s. | 100 g |
| pH 10. | |

This mixture, applied for 20 minutes at 28° C. to hair, gives it, after shampooing and rinsing, a colour:

on white-bleached hair on 90% naturally white hair 10 RP 3/10, according to the Munsell notation.

EXAMPLE 8

Direct dyeing

The following dye mixture is prepared:

| | |
|---|---|
| 4-amino-5,6-dimethyl-3-nitro-N—β-aminoethyl-aniline | 0.01 g |
| (4-N—β-hydroxyethylamino-3-nitro)phenyl β-hydroxyethyl ether | 0.25 g |
| 4-N'—β-hydroxyethylamino-3-nitro-N,N—di(β-hydroxyethyl) aniline | 0.20 g |
| 2-butoxyethanol | 10 g |
| CEMULSOL NP 4 - RHONE-POULENC Company (nonylphenol with 4 moles of ethylene oxide) | 12 g |
| CEMULSOL NP 9 - RHONE-POULENC COMPANY (nonylphenol with 9 moles of ethylene oxide) | 15 g |
| oleyl alcohol polyglycerolated with 2 moles of glycerol | 1.5 g |
| oleyl alcohol polyglycerolated with 4 moles of glycerol | 1.5 g |
| lactic acid | 0.5 g |
| water q s. | 100 g |
| pH 5. | |

This mixture, applied for 30 minutes at 30° C. to 90% naturally white hair, gives it, after shampooing and rinsing, a pink beige colour.

EXAMPLE 9

Oxidation dyeing

The following dye mixture is prepared:

| | |
|---|---|
| 4-amino-5,6-dimethyl-3-nitro-N—β,γ-dihydroxypropyl-aniline | 0.1 g |
| paraphenylenediamine | 0.05 g |
| paraaminophenol | 0.27 g |
| 4-N—methylaminophenol sulphate | 0.12 g |
| 2,4-diaminophenoxyethanol dihydrochloride | 0.017 g |
| resorcinol | 0.06 g |
| metaaminophenol | 0.055 g |
| 2-isopropyl-6-nitroaniline | 0.04 g |
| CEMULSOL NP 4 (nonylphenol with 4 moles of ethylene oxide, sold by RHONE-POULENC) | 21 g |
| CEMULSOL NP 9 (nonylphenol with 9 moles of ethylene oxide, sold by RHONE-POULENC) | 24 g |
| oleic acid | 4 g |
| 2-butoxyethanol | 3 g |
| 96° ethanol | 10 g |
| MASQUOL DTPA (sodium salt of diethylenetriamine pentacetic acid) | 2.5 g |
| thioglycolic acid | 0.6 g |
| 22° Be aqueous ammonia | 10 g |
| water q.s. | 100 g |
| pH 10.1. | |

100 g of 20-volume hydrogen peroxide are added at the time of use.

This mixture, applied for 20 minutes at 30° C. to permanent-waved hair, gives it, after shampooing and rinsing, a golden light chestnut colour.

EXAMPLE 10

Oxidation dyeing

The following dye composition is prepared:

| | |
|---|---|
| 4-amino-5,6-dimethyl-3-nitro-N—β-aminoethyl-aniline | 0.15 g |
| 3-N—methylamino-4-nitrophenyl β-hydroxyethyl ether | 0.2 g |
| paraphenylenediamine | 0.08 g |
| paraaminophenol | 0.1 g |
| resorcinol | 0.05 g |
| metaaminophenol | 0.15 g |
| carboxymethylcellulose | 2 g |
| ammonium laurylsulphate | 5 g |
| 2-butoxyethanol | 8 g |
| propylene glycol | 8 g |
| MASQUOL DTPA | 2 g |
| thioglycolic acid | 0.4 g |
| ammonium acetate | 1 g |
| 22° Be aqueous ammonia | 10 g |
| water q.s. | 100 g |
| pH 9.8. | |

100 g of 20-volume hydrogen peroxide are added at the time of use.

This mixture, applied to bleached hair for 25 minutes at 30° C., gives it, after rinsing and shampooing, a golden chestnut colour.

EXAMPLE 11

Direct dyeing

The following dye mixture is prepared:

| | |
|---|---|
| 4-amino-5,6-dimethyl-3-nitro-N—β-diethylaminoethyl-aniline | 0.25 g |
| 96° alcohol | 10 g |
| triethanolamine, 1% strength by weight | 3 g |
| CELLOSIZE W.P. 03 - UNION CARBIDE Company (hydroxyethylcellulose) | 2 g |
| ammonium laurylsulphate | 5 g |
| water q.s. | 100 g |
| pH 8.37. | |

This mixture, applied for 20 minutes at 28° C. to bleached hair, gives it, after shampooing and rinsing, a colour of 9 R 7/5 according to the MUNSELL notation.

EXAMPLE 12

Oxidation dyeing

The following dye mixture is prepared:

| | |
|---|---|
| 4-amino-5,6-dimethyl-3-nitro-N—β-diethylaminoethyl-aniline | 0.2 g |
| orthoaminophenol | 0.064 g |
| paraphenylenediamine | 0.3 g |
| paraaminophenol | 0.08 g |
| resorcinol | 0.15 g |
| metaaminophenol | 0.08 g |
| CEMULSOL NP 4 (nonylphenol oxyethylated with 4 moles of ethylene oxide, sold by RHONE-POULENC) | 12 g |
| CEMULSOL NP 9 (nonylphenol oxyethylated with 9 moles of ethylene oxide, sold by RHONE-POULENC) | 15 g |
| oleyl alcohol polyglycerolated with 2 moles of glycerol | 1.8 g |
| oleyl alcohol polyglycerolated with 4 moles of glycerol | 1.5 g |
| propylene glycol | 6 g |
| TRILON B (sodium salt of ethylenediamine tetracetic acid) | 0.12 g |
| 22° Be aqueous ammonia | 11 g |
| thioglycolic acid | 0.6 g |
| water q.s. | 100 g |
| pH 10.5. | |

An equal weight of 20-volume hydrogen peroxide is added at the time of use.

This mixture, applied for 25 minutes at 28° C. to permanent-waved hair, gives it, after shampooing and rinsing, a medium chestnut colour.

EXAMPLE 13

Direct dyeing

The following dye mixture is prepared:

| | |
|---|---|
| 4-amino-5,6-dimethyl-3-nitro-N—β-diethylaminoethyl-aniline | 0.05 g |
| 1,4,5,8-tetraaminoanthraquinone | 0.15 g |
| 2-methyl-4-amino-5-nitrophenol | 0.1 g |
| 2-butoxyethanol | 6 g |
| LAURAMIDE - WITCO Company (lauric acid monoethanolamide) | 1.5 g |
| lauric acid | 1 g |
| CELLOSIZE W.P. 03 - UNION CARBIDE Company (hydroxyethylcellulose) | 5 g |
| monoethanolamine | 2 g |
| water q.s. | 100 g |
| pH 9.5. | |

This mixture, applied for 30 minutes at 28° C. to 90% naturally white hair, gives it, after shampooing and rinsing, a sand colour.

EXAMPLE 14

Direct dyeing

The following dye composition is prepared:

| | |
|---|---|
| 5,6-dimethyl-3-nitroparaphenylenediamine | 0.15 g |
| 2-butoxyethanol | 15 g |
| copra fatty acids diethanolamides | 2.2 g |
| lauric acid | 0.8 g |
| ethylene glycol monoethyl ether | 2 g |
| monoethanolamine | 1 g |
| water q.s | 100 g |
| pH 7.0. | |

This mixture, applied for 25 minutes at 28° C. to white-bleached hair, gives it, after rinsing and shampooing, a salmon pink colour.

EXAMPLE 15

Direct dyeing

The following dye composition is prepared:

| | |
|---|---|
| 2,6-dimethyl-3-nitroparaphenylenediamine | 0.1 g |
| 2-butoxyethanol | 10 g |
| hydroxyethylcellulose | 2 g |
| ammonium laurylsulphate | 5 g |
| 1% strength triethanolamine solution | 2 g |
| water q.s. | 100 g |
| pH 8.4. | |

This mixture, applied for 20 minutes at 28° C. to white-bleached hair, gives it, after rinsing and shampooing, a pink champagne colour.

EXAMPLE 16

Direct dyeing

The following dye composition is prepared:

| | |
|---|---|
| 5,6-dimethyl-3-nitroparaphenylenediamine | 0.35 g |
| 2-amino-3-nitrophenol | 0.12 g |
| 3-nitro-4-N'—β-aminoethylamino-N,N—β-hydroxy-ethylaniline dihydrochloride | 0.15 g |
| 2-butoxyethanol | 10 g |
| ALFOL C$_{16/18E}$ (cetylstearyl alcohol sold by the CONDEA Company) | 8 g |
| Cire de Lanette E (sodium cetylstearyl sulphate, sold by HENKEL) | 0.5 g |
| CEMULSOL B (ethoxylated castor oil sold by RHONE-POULENC | 1 g |
| oleyl diethanolamide | 1.5 g |
| 22° Be aqueous ammonia | 2 g |
| water q.s | 100 g |
| pH 10.0. | |

This mixture, applied to bleached hair for 15 minutes at 25° C., gives it, after rinsing and shampooing, a red copper colour.

EXAMPLE 17

Direct dyeing

The following dye composition is prepared:

| | |
|---|---|
| 5,6-dimethyl-3-nitroparaphenylenediamine | 0.16 g |
| 2,6-dimethyl-5-nitroparaphenylenediamine | 0.3 g |
| 2-methyl-4-amino-5-nitrophenol | 0.2 g |
| 2-methyl-5-nitro-N,N'—β-hydroxyethylparaphenyl-enediamine | 0.08 g |
| 1,4,5,8-tetraaminoanthraquinone | 0.25 g |
| 2-butoxyethanol | 10 g |
| ALFOL C$_{16/18E}$ (cetylstearyl alcohol sold by the CONDEA Company) | 8 g |
| Cire de Lanette E (sodium cetylstearyl sulphate sold by HENKEL) | 0.5 g |
| CEMULSOL B (ethoxylated castor oil sold by RHONE-POULENC) | 1 g |
| oleyl diethanolamide | 1.5 g |
| 25% strength solution of 2-methyl-2-aminopropan-1-ol | 1 g |
| water q.s | 100 g |
| pH 9.8. | |

This mixture, applied for 20 minutes at 28° C. to permanent-waved, 90% white hair, gives it, after rinsing and shampooing, a coppery medium chestnut colour.

EXAMPLE 18

Direct dyeing

The following dye composition is prepared:

| | |
|---|---|
| 5,6-dimethyl-3-nitroparaphenylenediamine | 0.25 g |
| 2-methyl-6-nitroaniline | 0.1 g |
| 1,4,5,8-tetraaminoanthraquinone | 0.25 g |
| 96° alcohol | 20 g |
| hydroxyethylcellulose | 2 g |
| ammonium laurylsulphate | 5 g |
| 5% strength aqueous ammonia | 0.5 g |
| water q.s | 100 g |
| pH 8. | |

This mixture is applied for 15 minutes at 30° C. to permanent-waved 95% white hair; after rinsing and shampooing, it gives it a copper colour.

EXAMPLE 19

Direct dyeing

The following dye composition is prepared:

| | |
|---|---|
| 2,6-dimethyl-3-nitroparaphenylenediamine | 0.25 g |
| 3-nitro-4-N'—β-hydroxyethylamino-N—methyl- | 0.15 g |

-continued

| | |
|---|---|
| 2-N—β-hydroxyethylamino-5-nitroanisol aniline | 0.08 g |
| 2-butoxyethanol | 10 g |
| LAURAMIDE (lauric acid monoethanolamide sold by WITCO) | 1.5 g |
| lauric acid | 1 g |
| hydroxyethylcellulose | 5 g |
| monoethanolamine | 2 g |
| water q.s. | 100 g |
| pH 9.5. | |

This mixture, applied for 20 minutes at 28° C. to 90% naturally white hair, gives it, after rinsing and shampooing, a coppery light chestnut colour.

EXAMPLE 20

Oxidation dyeing

The following dye composition is prepared:

| | |
|---|---|
| paraphenylenediamine | 0.16 g |
| resorcinol | 0.1 g |
| metaaminophenol | 0.05 g |
| 2,4-diaminophenoxyethanol dihydrochloride | 0.03 g |
| 5,6-dimethyl-3-nitroparaphenylenediamine | 0.35 g |
| 2-methyl-5-nitro-N,N'—β-hydroxyethyl-paraphenylenediamine | 0.08 g |
| oleyl alcohol oxyethylated with 2 moles of ethylene oxide | 4.5 g |
| oleyl alcohol oxyethylated with 4 moles of ethylene oxide | 4.5 g |
| ETHOMEEN TO₁₂ (oleylstearylamine oxyethylated with 12 moles of ethylene oxide, sold by ARMAK) | 4.5 g |
| copra fatty acids diethanolamides | 9 g |
| propylene glycol | 4 g |
| 2-butoxyethanol | 8 g |
| 96° ethanol | 6 g |
| MASQUOL DTPA (sodium salt of diethylenetriamine pentacetic acid) | 2 g |
| hydroquinone | 0.15 g |
| 35° Be sodium bisulphite solution | 1.3 g |
| 22° Be aqueous ammonia | 10 g |
| water q.s. | 100 g |
| pH 10.5 | |

100 g of 20-volume hydrogen peroxide are added at the time of use.

This mixture, applied for 20 minutes at 25° C. to 90% naturally white hair, gives it, after rinsing and shampooing, a red chestnut colour.

EXAMPLE 21

Oxidation dyeing

The following dye composition is prepared:

| | |
|---|---|
| paraphenylenediamine | 0.2 g |
| 2,4-diaminophenoxyethanol dihydrochloride | 0.07 g |
| resorcinol | 0.2 g |
| metaaminophenol | 0.08 g |
| 2-methyl-5-N—β-hydroxyethylaminophenol | 0.07 g |
| paraaminophenol | 0.08 g |
| 2,6-dimethyl-3-nitroparaphenylenediamine | 0.22 g |
| CEMULSOL NP₄ (nonylphenol with 4 moles of ethylene oxide, sold by RHONE-POULENC) | 21 g |
| CEMULSOL NP₉ (nonylphenol with 9 moles of ethylene oxide, sold by RHONE-POULENC) | 24 g |
| oleic acid | 4 g |
| 2-butoxyethanol | 3 g |
| 96° ethanol | 10 g |
| MASQUOL DTPA | 2.5 g |
| 35° Be sodium bisulphite | 1 g |
| 22° Be aqueous ammonia | 10 g |
| water q.s. | 100 g |

-continued pH 10.5.

100 g of 20-volume hydrogen peroxide are added at the time of use.

This mixture, applied for 20 minutes at 30° C. to 90% naturally white hair, gives it, after rinsing and shampooing, a brown colour with purple-violet glints.

EXAMPLE 22

Oxidation dyeing

The following dye composition is prepared:

| | |
|---|---|
| paratolylenediamine dihydrochloride | 0.23 g |
| resorcinol | 0.12 g |
| 2-methyl-5-N—methylaminophenol | 0.08 g |
| paraaminophenol | 0.05 g |
| 2,6-dimethyl-3-nitroparaphenylenediamine | 0.4 g |
| ALFOL C₁₆/₁₈E (cetylstearyl alcohol sold by the CONDEA Company) | 8 g |
| Cire de Lanette E (sodium cetylstearyl sulphate sold by HENKEL) | 0.5 g |
| CEMULSOL B (ethoxylated castor oil sold by RHONE-POULENC) | 1 g |
| oleyl diethanolamide | 1.5 g |
| MASQUOL DTPA | 2.5 g |
| mercaptosuccinic acid | 0.3 g |
| 22° Be aqueous ammonia | 11 g |
| water q.s. | 100 g |
| pH 10.5. | |

100 g of 20-volume hydrogen peroxide are added at the time of use.

This mixture applied for 25 minutes at 25° C. to white-bleached hair, gives it, after rinsing and shampooing, a mahogany colour.

EXAMPLE 23

Oxidation dyeing

The following dye composition is prepared:

| | |
|---|---|
| 5,6-dimethyl-3-nitroparaphenylenediamine | 0.045 g |
| paraphenylenediamine | 0.03 g |
| resorcinol | 0.06 g |
| paraaminophenol | 0.02 g |
| hydroxyethylcellulose | 2 g |
| ammonium laurylsulphate | 5 g |
| 2-butoxyethanol | 15 g |
| 96° alcohol | 5 g |
| 20% strength aqueous ammonia | 10 g |
| 35° Be sodium bisulphite | 1 g |
| hydroquinone | 0.15 g |
| water q.s. | 100 g |
| pH 10.3 | |

75 g of 20-volume hydrogen peroxide are added at the time of use.

This mixture, applied for 25 minutes at 20° C. to bleached hair, gives it, after rinsing and shampooing, a golden sand colour.

EXAMPLE 24

Oxidation dyeing

The following dye composition is prepared:

| | |
|---|---|
| 5,6-dimethyl-3-nitroparaphenylenediamine | 0.2 g |
| N,N—di-β-hydroxyethylparaphenylenediamine dihydrochloride | 0.08 g |
| paraaminophenol | 0.15 g |

| -continued | |
|---|---|
| 2-methyl-5-N—β-hydroxyethylaminophenol | 0.1 g |
| resorcinol | 0.16 g |
| 4-N'—β-hydroxyethylamino-3-nitro-N—methyl-N—β-hydroxyethylaniline | 0.1 g |
| hydroxyethylcellulose sold under the name CELLOSIZE W.P. 03 by UNION CARBIDE | 2 g |
| ammonium laurylsulphate | 5 g |
| 2-butoxyethanol | 15 g |
| 96° alcohol | 5 g |
| MASQUOL DTPA | 2 g |
| hydroquinone | 0.15 g |
| sodium bisulphite solution, d = 1.32 | 1.5 g |
| monoethanolamine | 8 g |
| water q.s. | 100 g |
| pH 10.7. | |

80 g of 20-volume hydrogen peroxide are added at the time of use.

This mixture, applied for 25 minutes at 25° C. to bleached hair, gives it, after rinsing and shampooing, a coral colour.

EXAMPLE 25

Oxidation dyeing

The following dye composition is prepared:

| | |
|---|---|
| 2,6-dimethyl-3-nitroparaphenylenediamine | 0.2 g |
| 2,6-dimethylparaphenylenediamine dihydrochloride | 0.1 g |
| 2,4-diaminophenoxyethanol dihydrochloride | 0.04 g |
| resorcinol | 0.11 g |
| metaaminophenol | 0.06 g |
| 2-methyl-5-N—β-hydroxyethylaminophenol | 0.05 g |
| paraaminophenol | 0.05 g |
| REMCOPAL 334 (nonylphenol with 4 moles of ethylene oxide, sold by GERLAND) | 21 g |
| REMCOPAL 349 (nonylphenol with 9 moles of ethylene oxide, sold by GERLAND) | 24 g |
| oleic acid | 4 g |
| 2-butoxyethanol | 3 g |
| 96° alcohol | 10 g |
| MASQUOL DTPA | 2.5 g |
| 35° Be sodium bisulphite | 1 g |
| hydroquinone | 0.12 g |
| 22° Be aqueous ammonia | 10 g |
| water q.s. | 100 g |
| pH 10.6 | |

100 g of 20-volume hydrogen peroxide are added at the time of use.

This mixture, applied for 20 minutes at 28° C. to bleached hair, gives it, after rinsing and shampooing, a tin-grey colour with pink glints.

EXAMPLE 26

Oxidation dyeing

The following dye composition is prepared:

| | |
|---|---|
| 5,6-dimethyl-3-nitroparaphenylenediamine | 0.25 g |
| N—β-methoxyethylparaphenylenediamine dihydrochloride | 1 g |
| paraaminophenol | 0.3 g |
| resorcinol | 0.25 g |
| metaaminophenol | 0.15 g |
| hydroquinone | 0.15 g |
| nonylphenol oxyethylated with 9 moles of ethylene oxide | 3 g |
| oleyl alcohol | 9 g |
| oleyl diethanolamide | 9 g |
| hydrogenated tallow amide with 50 moles of ethylene oxide | 2.5 g |
| oleic acid | 18 g |
| cationic polymer containing the repeat unit: | 3 g |

| -continued | |
|---|---|
| 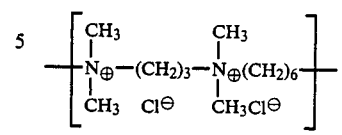 | |
| ethyl alcohol | 9 g |
| benzyl alcohol | 11 g |
| ethylene diamine tetracetic acid | 0.2 g |
| 22° Be aqueous ammonia | 14 g |
| monoethanolamine | 6.5 g |
| 35° Be sodium bisulphite | 1.3 g |
| water q.s. | 100 g |

This liquid composition gives a creamy gel when diluted with an equal weight of 20-volume hydrogen peroxide.

When this gel is applied for 30 minutes to dark blonde hair and when a shampoo is finally applied, there is obtained, after drying, a hair colour which is coppery red light blonde.

The nitro colorant employed, namely 5,6-dimethyl-3-nitroparaphenylenediamine, is stable in the liquid composition.

EXAMPLE 27

Oxidation dyeing

The following dye composition is prepared:

| | |
|---|---|
| 2,6-dimethyl-3-nitroparaphenylenediamine | 0.4 g |
| paraphenylenediamine | 0.35 g |
| 2-chloroparaphenylenediamine | 0.10 g |
| paraaminophenol | 0.10 g |
| resorcinol | 0.20 g |
| metaaminophenol | 0.30 g |
| 2-methylresorcinol | 0.20 g |
| hydroquinone | 0.15 g |
| oleyl alcohol glycerolated with 2 moles of glycerol | 5 g |
| oleyl alcohol glycerolated with 4 moles of glycerol | 5 g |
| oleic acid | 5 g |
| oleyl diethanolamide | 5 g |
| oleyl diethanolamide | 12 g |
| ethyl alcohol | 10 g |
| 2-ethoxyethanol | 12 g |
| ethylenediamine tetracetic acid | 0.2 g |
| 35° Be sodium bisulphite | 1.3 g |
| 22° Be aqueous ammonia | 8 g |
| monoethanolamine | 3 g |
| water q.s. | 100 g |

This liquid is diluted at the time of use with an equal weight of an oxidising lotion which titrates for 20 volumes of hydrogen peroxide. The gel obtained is applied for 30 minutes to chestnut hair and rinsing is carried out. A shampoo is applied and the hair is dried. Hair which is dyed to a coppery dark blonde shade is then obtained.

It is found that in this composition, the nitro colorant, namely 2,6-dimethyl-3-nitroparaphenylenediamine is preserved.

We claim:

1. Dimethyl derivative of 3-nitro-4-aminoaniline, having the following formula (I):

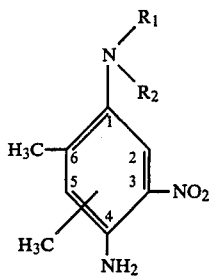

(I)

in which the radical CH₃ of a variable position is in position 2 or 5 of the benzene ring and $R_1$ and $R_2$ denote, independently of each other, a hydrogen atom, a lower alkyl group, a lower mono- or polyhydroxyalkyl group or lower aminoalkyl group in which the amino group is optionally mono- or disubstituted by a lower alkyl radical or by a lower mono- or polyhydroxyalkyl radical, it being understood that the two symbols $R_1$ and $R_2$ can be simultaneously other than hydrogen only when the mobile CH₃ radical is in position 5, and cosmetically acceptable salts of this compound.

2. Compound according to claim 1, wherein
  at least one of the radicals $R_1$ and $R_2$ denotes a hydrogen atom.

3. Compound according to claim 1 which is chosen from the group consisting of: 2,6-dimethyl-3-nitroparaphenylenediamine, 5,6-dimethyl-3-nitroparaphenylenediamine, 4-amino-2,6-dimethyl-3-nitro-N-methylaniline, 4-amino-5,6-dimethyl-3-nitro-N-β-hydroxyethylaniline, 4-amino-5,6-dimethyl-3-nitro-N-β,γ-dihydroxypropylaniline, 4-amino-5,6-dimethyl-3-nitro-N-β-aminoethylaniline, and 4-amino-5,6-dimethyl-3-nitro-N-β-diethylaminoethylaniline.

4. Dyeing composition for keratinic fibres, which comprises, in a solvent medium, a quantity which is effective for dyeing, of at least one compound such as defined in claim 1.

5. Composition according to claim 4, intended for dyeing human hair, which comprises in a cosmetically acceptable medium, at least one compound of formula (I) in proportions of from 0.001 to 5% by weight, and preferably between 0.05 and 2% by weight relative to the total weight of the composition.

6. Composition according to claim 4 which has a pH of between 3 and 11.5.

7. Dyeing composition according to claim 4 wherein the solvents are chosen from the group consisting of water, lower alkanols, aromatic alcohols, polyols, and their ethers or their mixtures.

8. Composition according to claim 4 which additionally comprises cosmetic adjuvants chosen from the group comprising anionic, cationic, nonionic or amphoteric surface-active agents or their mixtures, thickeners, dispersing agents, penetrating agents, sequestering agents, film-forming agents, buffers, perfumes, and alkalising or acidifying agents.

9. Composition according to claim 4 intended to be employed for direct colouring of human hair, which contains, in addition, other direct colorants chosen from the group consisting of azo colorants, anthraquinone colorants and nitro derivatives of the benzene series other than those of formula (I).

10. Composition according to claim 4, intended to be employed as a hair-setting lotion, which takes the form of an aqueous, alcoholic or aqueous alcoholic solution containing at least one cosmetic resin.

11. Composition according to claim 4, intended to be employed for oxidation dyeing, which additionally comprises at least one precursor of an oxidation colorant.

12. Composition according to claim 11, which has a pH of between 7 and 11.5 and additionally contains a reducing agent.

13. A process for colouring keratinic fibres, wherein an effective quantity of a composition as defined in claim 9 is applied to the fibres, is left in place for 5 to 50 minutes, followed by rinsing, washing if appropriate, rinsing again and drying.

14. Process for colouring keratinic fibres, wherein an effective quantity of a composition as defined in claim 10 is applied to the washed and rinsed fibres, which are wound if appropriate and dried.

15. Process for colouring keratinic fibres, wherein an effective quantity of a composition as defined in claim 11, optionally with the addition of an oxidising agent, is applied to the fibres, is left for 10 to 50 minutes, followed by rinsing, washing with a shampoo if appropriate, rinsing again and drying.

* * * * *